(12) United States Patent
Luco

(10) Patent No.: US 9,545,332 B2
(45) Date of Patent: Jan. 17, 2017

(54) CUSPID AND FIRST BI-CUSPID BITE RETAINER FOR SLEEP APNEA

(71) Applicant: Kenneth Luco, Kingston (CA)

(72) Inventor: Kenneth Luco, Kingston (CA)

(*) Notice: Subject to any disclaimer, the term of this patent is extended or adjusted under 35 U.S.C. 154(b) by 49 days.

(21) Appl. No.: 14/866,964

(22) Filed: Sep. 27, 2015

(65) Prior Publication Data

US 2016/0015556 A1    Jan. 21, 2016

(51) Int. Cl.
*A61F 5/56* (2006.01)

(52) U.S. Cl.
CPC ..................... *A61F 5/566* (2013.01)

(58) Field of Classification Search
CPC ....................................... A61F 5/566
See application file for complete search history.

(56) References Cited

U.S. PATENT DOCUMENTS

| | | |
|---|---|---|
| 3,967,379 A | 7/1976 | Bergersen |
| 3,991,471 A | 11/1976 | Hoops |
| 3,994,068 A | 11/1976 | Goshgarian |
| 4,073,061 A | 2/1978 | Bergersen |
| 4,272,240 A | 6/1981 | Glassman |
| 4,299,568 A | 11/1981 | Crowley |
| 4,318,694 A | 3/1982 | Klein |
| 4,354,834 A | 10/1982 | Wilson |
| 4,371,336 A | 2/1983 | Hilleman |
| 4,398,884 A | 8/1983 | Huffman |
| 4,468,196 A | 8/1984 | Keller |
| 4,533,320 A | 8/1985 | Piekarsky |
| 4,571,179 A | 2/1986 | Balenseifen |
| 4,609,350 A | 9/1986 | Krause |
| 4,655,707 A | 4/1987 | Chasanoff |
| 4,676,752 A | 6/1987 | Lefkowitz |
| 4,723,910 A | 2/1988 | Keller |
| 4,894,012 A | 1/1990 | Goldberg |
| 4,901,737 A | 2/1990 | Toone |
| 4,909,738 A | 3/1990 | Ai |
| 4,986,283 A | 1/1991 | Tepper |
| 5,052,409 A | 10/1991 | Tepper |
| 5,083,919 A | 1/1992 | Quach |
| 5,376,001 A | 12/1994 | Tepper |
| 5,527,182 A | 6/1996 | Willoughby |
| 5,580,243 A | 12/1996 | Bloore |
| 5,630,715 A | 5/1997 | Voudouris |
| 5,697,781 A | 12/1997 | Ellingson |
| 5,735,692 A | 4/1998 | Berger |
| 5,861,001 A | 1/1999 | Katsev |
| 5,873,721 A | 2/1999 | Willoughby |
| 5,913,680 A | 6/1999 | Voudouris |
| 6,126,445 A | 10/2000 | Willoughby |

(Continued)

*Primary Examiner* — Tarla Patel
(74) *Attorney, Agent, or Firm* — Michael J. Feigin, Esq.; Feigin & Fridman

(57) ABSTRACT

A retainer with a block extending downwards from an otherwise generally flat surface is disclosed. The block corresponds to a region of one or more of the cuspids or pre-molars. A side block or other device on the upper retainer also abuts a wing or other abutment device of a lower retainer, causing the lower jaw to be pushed forward relative to the upper jaw and resting position (regular organic closing position) of the upper and lower jaw together. Thus, the upper teeth are pushed forward and a space is created between the teeth behind the (lower) block preventing an apnea during sleep.

17 Claims, 9 Drawing Sheets

(56) References Cited

U.S. PATENT DOCUMENTS

| | | |
|---|---|---|
| 6,168,428 B1 | 1/2001 | Voudouris |
| 6,257,883 B1 | 7/2001 | Voudouris |
| 6,283,753 B1 | 9/2001 | Willoughby |
| 6,604,527 B1 * | 8/2003 | Palmisano ............... A61C 7/08 |
| | | 128/848 |
| 6,766,802 B1 | 7/2004 | Keropian |
| 6,790,036 B2 | 9/2004 | Graham |
| 6,913,460 B2 | 7/2005 | Cleary |
| 6,935,859 B2 | 8/2005 | White |
| 6,939,133 B2 | 9/2005 | Voudouris |
| 7,637,262 B2 | 12/2009 | Bailey |
| 7,730,891 B2 | 6/2010 | Lamberg |
| 8,297,970 B2 | 10/2012 | Kanomi |
| 8,500,446 B2 | 8/2013 | Lowe |
| 8,738,165 B2 | 5/2014 | Cinader |
| 8,827,696 B1 | 9/2014 | Sandwick |
| 8,827,697 B2 | 9/2014 | Cinader |
| 8,939,762 B2 | 1/2015 | Lowe |
| 8,986,003 B2 | 3/2015 | Valoir |
| 2005/0028826 A1 * | 2/2005 | Palmisano ............... A61F 5/566 |
| | | 128/848 |
| 2011/0220125 A1 * | 9/2011 | Van Dyke ................ A61F 5/566 |
| | | 128/848 |
| 2012/0227750 A1 * | 9/2012 | Tucker .................... A61F 5/566 |
| | | 128/848 |
| 2013/0112210 A1 * | 5/2013 | Stein ....................... A61F 5/566 |
| | | 128/848 |
| 2015/0075540 A1 * | 3/2015 | Dye ........................ A61F 5/566 |
| | | 128/848 |

* cited by examiner

CUSPID AND FIRST BI-CUSPID BITE RETAINER FOR SLEEP APNEA

FIELD OF THE DISCLOSED TECHNOLOGY

The disclosed technology relates generally to mouth retainers, and more specifically to one with a bite region at the cuspid and first bi-cuspid.

BACKGROUND OF THE DISCLOSED TECHNOLOGY

There are three forms of sleep apnea: central (CSA), obstructive (OSA), and complex or mixed sleep apnea (i.e., a combination of central and obstructive) constituting 0.4%, 84% and 15% of cases, respectively. In CSA, breathing is interrupted by a lack of respiratory effort; in OSA, breathing is interrupted by a physical block to airflow despite respiratory effort, and snoring is common. Referring now to OSA, more than 12 million American adults have obstructive sleep apnea. It is a disorder in which breathing is repeatedly, but briefly, interrupted during sleep. Obstructive sleep apnea occurs when the muscles in the back of the throat fail to keep the airway open, making it difficult to breathe. It is more common in people who are overweight, but it can affect anyone. For example, some small children may have obstructive sleep apnea due to enlarged tonsil tissue in their throats. For those with OSA, the airway collapses or becomes blocked during sleep. This causes shallow breathing, or pauses in breathing, which leads to fragmented sleep and low blood oxygen levels. OSA is commonly accompanied by snoring, as well. This is referred to as Upper Airway Restrictive Syndrome (UARS) and may also derive from medical conditions such as deviated septum, large turbinates, narrow palate, long soft palate etc. This condition is considered to be the same as OSA and is diagnosed and treated similarly. Sleep bruxism is another sleep disorder that occurs concurrently with OSA in a majority of patients. This is forceful side to side, front to back or vertical clenching and unclenching of the mandible. This can occur in all age groups and occurs in the general population at a frequency of between 8% and 26%.

Some patients with obstructive or other types of sleep apnea may benefit from surgery. The type of surgery depends on the cause of the sleep apnea. Examples for common types of surgical procedures for sleep apnea include removing the tonsils and adenoids, if these organs are blocking the airway. This can be especially helpful in the case of children. In advanced, non-responsive cases, the mandible may be broken and lengthened, to move the tongue out of the throat region. Another surgery involves placing a small hole and tube in the windpipe, causing airflow through the tube into the lungs. This is carried out in severe cases of sleep apnea. In still other cases, the uvula (the tissue that hangs down in the middle of the back of the throat), and part of the roof of the mouth at the back of the throat may be removed.

Another common treatment for sleep apnea, which does not require invasive surgery, is called continuous positive airway pressure (CPAP). In this treatment, the patient wears a special mask over nose and mouth (or inserts into the nose) while sleeping. The mask keeps the wearer's airway open by increasing the air pressure breathed in by the wearer. However, such masks cover a large portion of the face and head, are generally uncomfortable, and may leak or can fall off, thus reducing effectiveness. They do not treat sleep bruxism.

Still further, devices of the prior art have been designed to aid in obstructive sleep apnea problems. U.S. Pat. No. 5,427,117, issued to Thornton et al., discloses a dental device which includes adjustable upper and lower arch trays. The device has an upper arch and lower arch with an adjustable post that extends from the upper arch and contacts the lower arch, so that the user's lower jaw is extended forward with respect to the upper. The post shown in these references is shaped to engage with the lower arch, so that the user's mouth cannot be opened more than a predetermined amount while the post is engaged.

Still another device has been described in U.S. Pat. No. 5,829,441 issued to Kidd et al., which discloses a mandible extension dental device including adjustable upper and lower arch trays. Each upper and lower arch tray includes a U-shaped tray body attached to the upper and lower teeth. The device is adjusted to selectively cause extension of the user's lower jaw when the mouth is closed. The upper and lower trays dovetail with a depending hook located in the front of the device.

U.S. Pat. No. 6,766,802, issued to Keropian et al., discloses an appliance that covers the inside of the upper teeth only with an open palate similar to an upper orthodontic retainer. This device further has a retainer wire to hold the anterior teeth in place, or to move such teeth backwards, and a raised strip that extends from an incisor tip (biting edge) of central incisors to separate the posterior teeth and hold the tongue down.

Another device, the ALF (Advanced Lightwire Functionals) appliance is a cemented expansion appliance for orthodontic treatment. These devices are cemented with bands around the first molars with a wire custom bent to fit the teeth. Activation of the wire expands a plate. Another device is to a type of removable retainer that actively moves the teeth for final positioning. This appliance completely covers the teeth and does not have a definitive bite.

Thus, while there are many different ways of attempting to alleviate problems associated with OSA, there is still room for improvement. There is a need in the field to find devices which are least obtrusive, more comfortable, easy to use, durable, and most effective.

SUMMARY OF THE DISCLOSED TECHNOLOGY

In an embodiment of the disclosed technology, an upper and lower retainer (defined as "a device which snugly abuts teeth and can be removed therefrom") are used. An upper retainer is adapted for abutment against upper teeth, the upper retainer having a generally flat and elongated lower surface adapted to cover molars. The upper retainer further has lower blocks extending further downwards than the generally flat and elongated lower surface, forming its own lowest surface of the device and adapted to cover canine and first bicuspid teeth.

The lower retainer is adapted for (defined as "shaped in a way that the foregoing function is carried out readily and easily with the device") abutment against lower teeth, the lower retainer having a generally flat and elongated upper surface adapted to cover one or more of, or all of canine, cuspid, first and second bicuspid, and molars. Wings can extend from the lower retainer towards the upper retainer adapted to abut respective side blocks on exterior sides of the upper retainer.

The upper retainer and lower retainer can abut each other by way of contact between the lower blocks and the generally flat and elongated upper surface. A space can be formed between the upper retainer and the lower retainer at a region corresponding to the molars and the second bicuspid. The lower retainer further can have wings extending perpendicularly to the generally flat and elongated upper surface. The wings can abut respective side blocks jutting outwards from the upper retainer's side walls. The wings can have a front side perpendicular to the generally flat and elongated lower surface.

A wire on each of the upper retainer and the lower retainer covers at least the incisors, in embodiments of the disclosed technology. This wire connects left and right elongated regions (with flat upper or lower sides) together.

Described another way, the upper retainer has a metal wire adapted to cover incisors and connect left and right sides of the retainer. Each left and right side of the retainer has two generally flat regions on a bottom side. A rear region is adapted to cover at least molars and a front region is adapted to cover at least the first bicuspid and part of the cuspid, the front region extending lower from the teeth than the rear region. The front region and rear region can be separated at a vertically extending region which is perpendicular or generally so to the front and rear region. A side block, located at each rear region, has a flat front side extending outwards from the rear region. The front region has a generally flat lower surface, the generally flat lower surface forming a lowest side of the retainer for upper teeth.

Described yet another way, a retainer system with abutting upper retainer and lower retainer has a spaced apart region between areas of the upper retainer and the lower retainer corresponding to molars of the teeth that the retainers are adapted to cover. The retainer system can have contact points between the upper retainer and the lower retainer at regions corresponding to a first bi-cuspid of the upper teeth.

The spaced apart region further, in embodiments, has a region corresponding to a second bi-cuspid. The contact points can have a region corresponding to the cuspids. The lower retainer can have vertically extending wings. The upper retainer can have blocks extending outwards at a spaced apart region, each with a generally flat front surface. Each wing of the wings can abut a generally flat front surface of a block of the respective blocks. Contact points (which contact the lower retainer) of the upper retainer are at a lowest most extremity of the upper retainer at a block extending downwards further than a rest of the upper retainer. These contact points of the lower retainer can be on one of two generally flat elongated surfaces extending from a wire to an area corresponding to a molar.

Embodiments described with reference to the device of the disclosed technology are equally applicable to methods of use thereof.

"Substantially," "substantially shown," "and "generally" for purposes of this specification, are defined as "at least 90%," or as otherwise indicated. Any device can "comprise" or "consist of" the devices mentioned there-in, as limited by the claims. Any device recited in the specification is within an acceptable tolerance level known in the art, exactly as defined, and/or substantially as described.

It should be understood that the use of "and/or" is defined inclusively such that the term "a and/or b" should be read to include the sets: "a and b," "a or b," "a," "b."

DETAILED DESCRIPTION OF EMBODIMENTS OF THE DISCLOSED TECHNOLOGY

A retainer with a block extending downwards from an otherwise generally flat surface is disclosed. The block corresponds to a region of one or more of the cuspids or pre-molars. A side block or other device on the upper retainer also abuts a wing or other abutment device of a lower retainer causing the lower jaw to be pushed forward relative to the upper jaw and resting position (regular organic closing position) of the upper and lower jaw together. Thus, the upper teeth are pushed forward and a space is created between the teeth behind the (lower) block preventing an apnea during sleep.

Embodiments of the disclosed technology will become clearer in view of the following description of the drawings.

References to direction (e.g. "top" or "up", and "bottom" or "down"), for purposes of this specification refer to the direction when the retainers are worn by a person. For example, the "upper" retainer is worn above the "lower" retainer and each on the upper and lower teeth of a person, respectively. The lower side of the upper retainer is therefore the side adjacent to the lower retainer, and the upper side of the lower retainer is the side adjacent to the upper retainer. Further, for purposes of this specification, descriptions of portions of the retainer refer to both the right and left sides of the retainer or person wearing the retainer.

Figure 1:
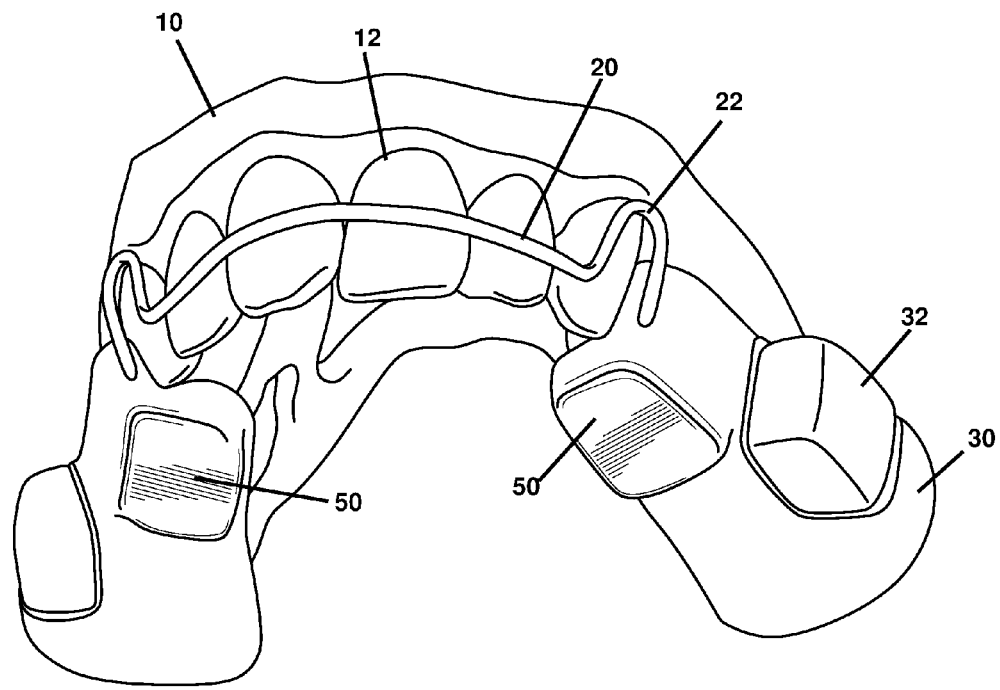
FIG. 1 shows a lower perspective view of an upper retainer of an embodiment of the disclosed technology.
Figure 2:
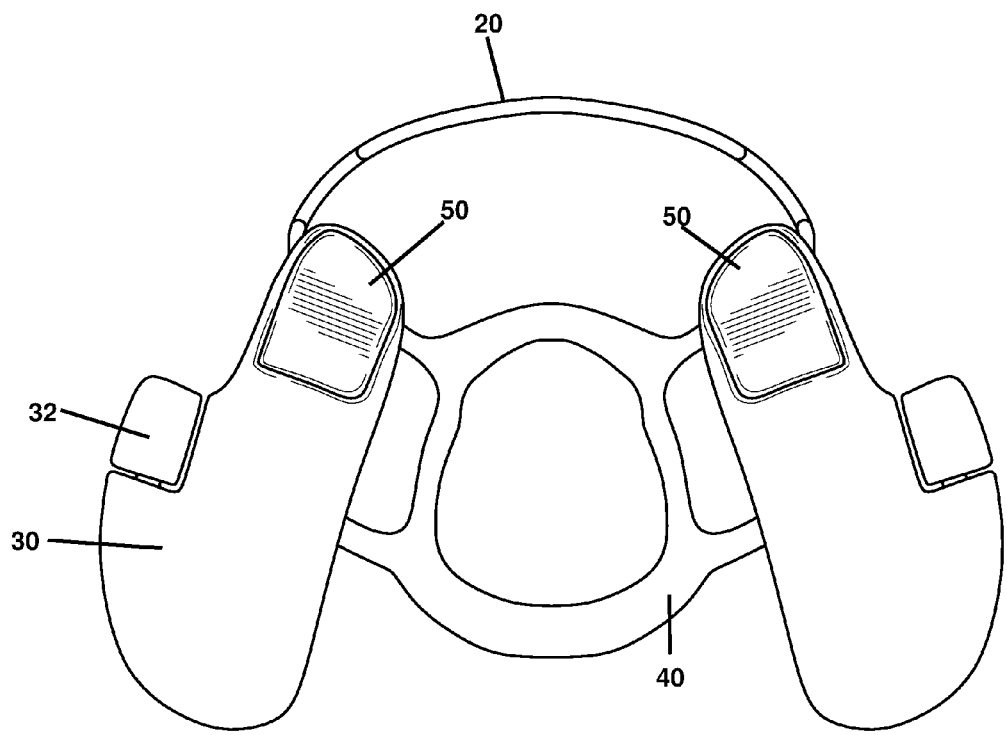
FIG. 2 shows a bottom plan view of the upper retainer of FIG. 1.
Figure 3:
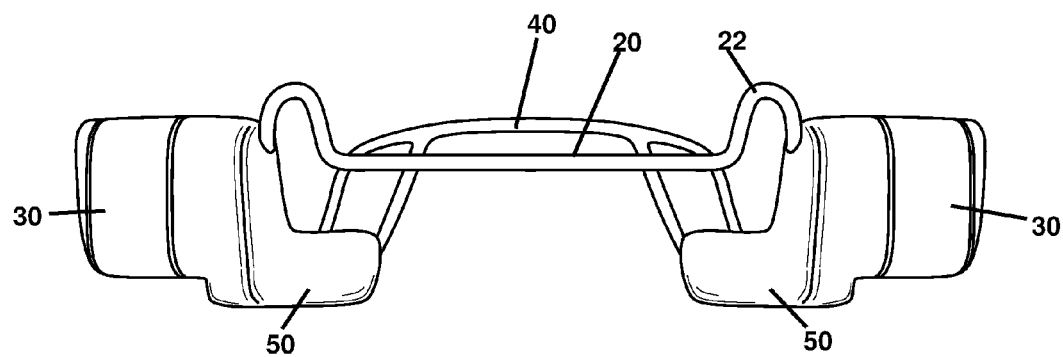
FIG. 3 shows a front elevation view of the upper retainer of FIG. 1.
Figure 4:
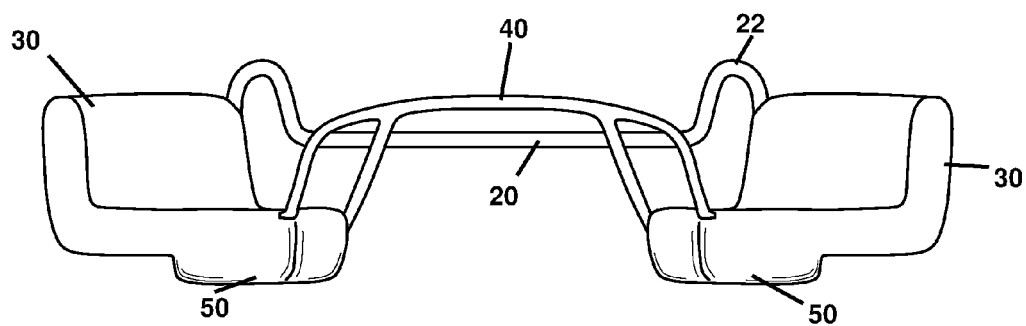
FIG. 4 shows a rear elevation view of the upper retainer of FIG. 1.
Figure 5:
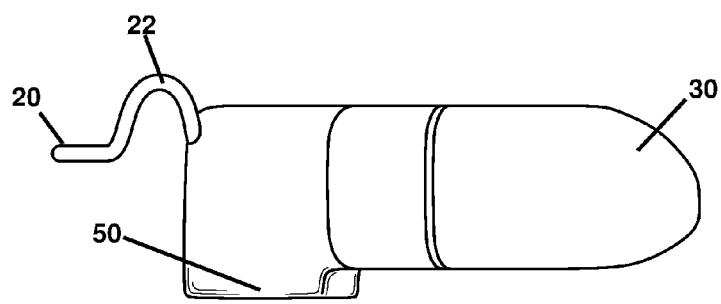
FIG. 5 shows a side elevation view of the upper retainer of FIG. 1.

Discussing FIGS. 1-4 showing the upper retainer, FIG. 1 shows a lower perspective view of an upper retainer of an embodiment of the disclosed technology. FIG. 2 shows a bottom plan view of the upper retainer of FIG. 1. FIG. 3 shows a front elevation view of the upper retainer of FIG. 1. FIG. 4 shows a rear elevation view of the upper retainer of FIG. 1. FIG. 5 shows a side elevation view of the upper retainer of FIG. 1. Here the upper mouth 10 has teeth 12. The teeth shown are the central incisor, lateral incisor, and canine of the upper jaw. A wire 20 with omega loop 22 is shown connecting two sides of the retainer together. This is what's known in the art as a "Hawley Retainer" or can be an "Essix" retainer (vacuum formed). The materials used can be metal, plastic, or others known in the art.

Here, the lower side of the upper retainer has a generally flat elongated side which corresponds to and covers at least the molars or a molar of the upper teeth. The generally flat elongated portion of the upper retainer can cover all of the third molar, second molar, first molar, second bicuspid, and first bicuspid. A lower block 50 can have a flat side which is lower than the generally flat elongated portion of the upper retainer. This block can extend, with perpendicular or generally perpendicular sides, down from the generally flat elongated portion (rest of the lower side covering the teeth) of the upper retainer to form a lowest generally flat or flat elongated side of the upper retainer. In this manner, the lower block 50 becomes the point of contact (on the side where the line extending from the number 50 reaches) between the upper retainer and the lower retainer (to be described). This leaves a space between the rest of the generally flat elongated portion 30 of the upper retainer and a lower retainer when the lower block 50 abuts a lower retainer. The lower block 50, in embodiments of the disclosed technology, corresponds to a cuspid and/or first bi-cuspid. That is, the lower block 50 can cover a cuspid, a bi-cuspid, or both a cuspid and bi-cuspid. This means that the respective tooth is situated directly above the block 50 which is covered by, corresponds with, and/or is adapted for covering the mentioned tooth.

Referring still to the upper retainer, side blocks 32 have right/perpendicular angles to the elongated flat region 30. The blocks 32 have a flat front side ("front" being relative to the front of a person wearing the retainer) which rises vertically or generally vertically. The blocks 32 further have a flat or generally flat bottom side (again, relative to the direction of a standing person wearing the device/the body of a person wearing the device). This block, in embodiments, abuts at its front side a flange or wing extending vertically upwards or upwards from a lower retainer.

Figure 6:
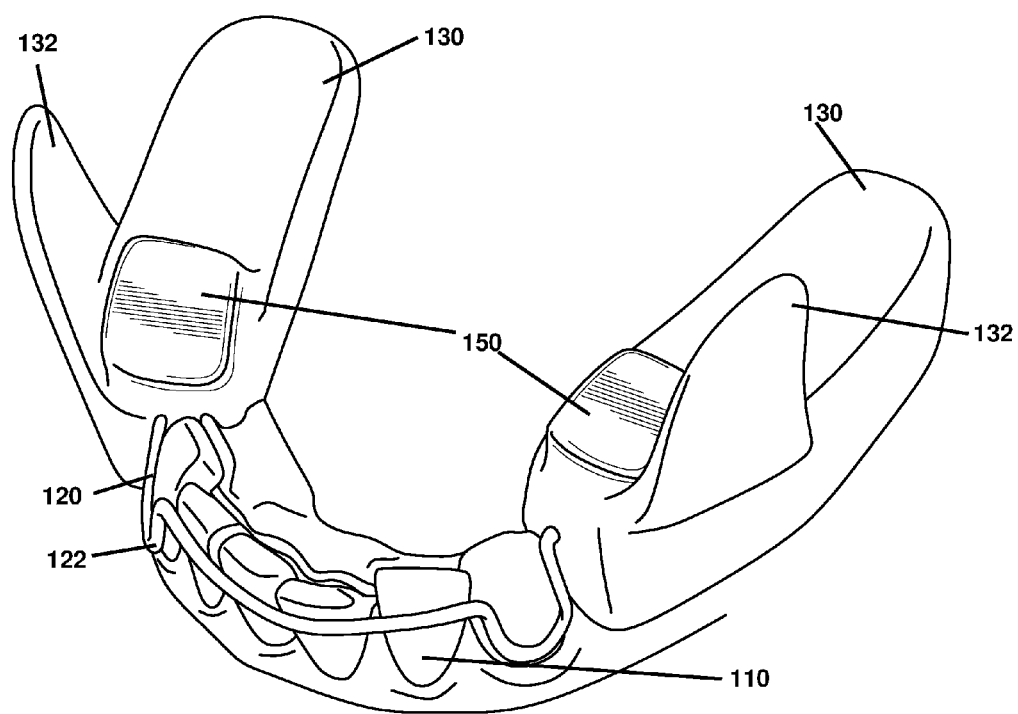
FIG. 6 shows an upper perspective view of a lower retainer of an embodiment of the disclosed technology.
Figure 7:
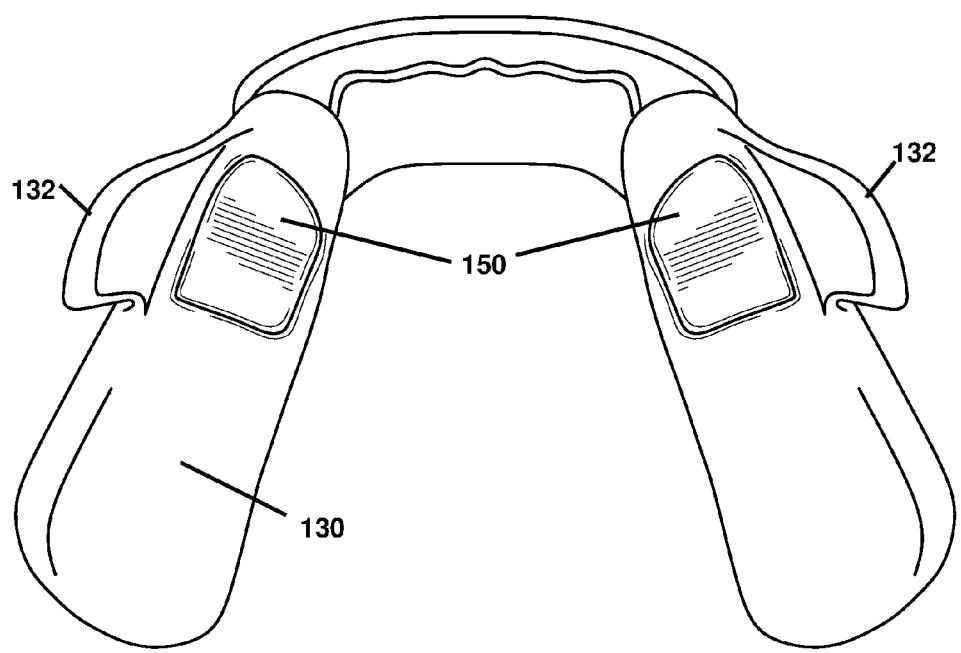
FIG. 7 shows a top plan view of the lower retainer of FIG. 6.
Figure 8:
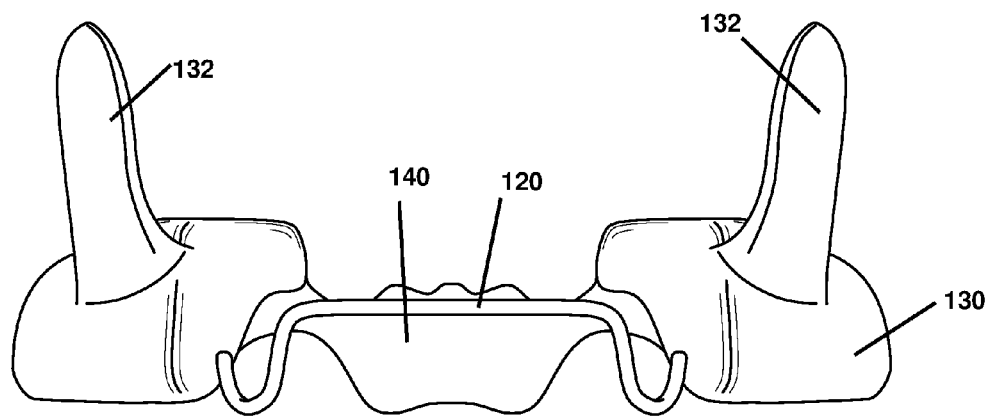
FIG. 8 shows a front elevation view of the lower retainer of FIG. 6.
Figure 9:
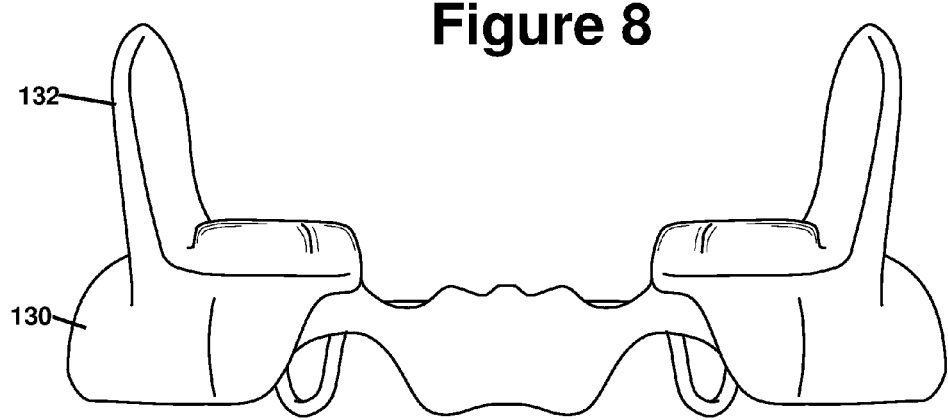
FIG. 9 shows a rear elevation view of the lower retainer of FIG. 6.
Figure 10:
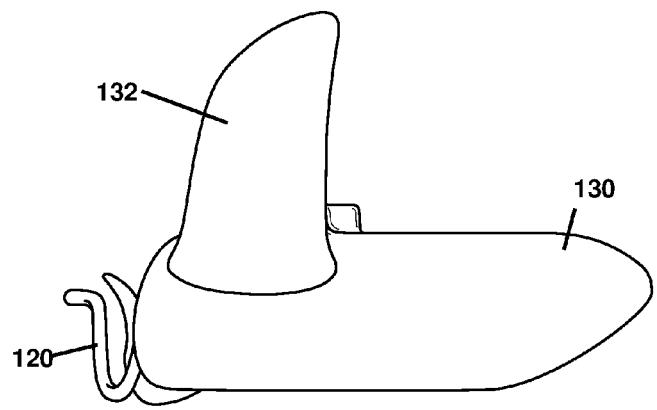
FIG. 10 shows a side elevation view of the lower retainer of FIG. 6.

Discussing now the lower retainer, elements of the upper retainer have been incremented by 100. FIG. 6 shows an upper perspective view of a lower retainer of an embodiment of the disclosed technology. FIG. 7 shows a top plan view of the lower retainer of FIG. 6. FIG. 8 shows a front elevation view of the lower retainer of FIG. 6. FIG. 9 shows a rear elevation view of the lower retainer of FIG. 6. FIG. 10 shows a side elevation view of the lower retainer of FIG. 6. The upper blocks 150 shown in FIGS. 6 and 7 are present in some embodiments; in other embodiments, the upper blocks are lacking and the generally flat elongated upper side extends the length of the material covering the teeth from the third molar to the canine, first bi-cuspid, or second bi-cuspid. As such, the lower block 50 of the upper retainer contacts the generally flat elongated upper side 130 (or block 150, if present) of the lower retainer. This occurs when one bites down, pushing the upper and lower retainers against each other, whether while awake or asleep.

The lower retainer has two flanges or wings 132 in embodiments of the disclosed technology. These wings rise at a 90 degree angle or substantially a 90 degree angle to the generally flat elongated side 130 of the lower retainer. The rear side (relative to the position when worn by a user) of the flange 132 abuts the side block 32 of the upper retainer when worn, pushing the lower teeth forward and preventing an apnea.

Figure 11:
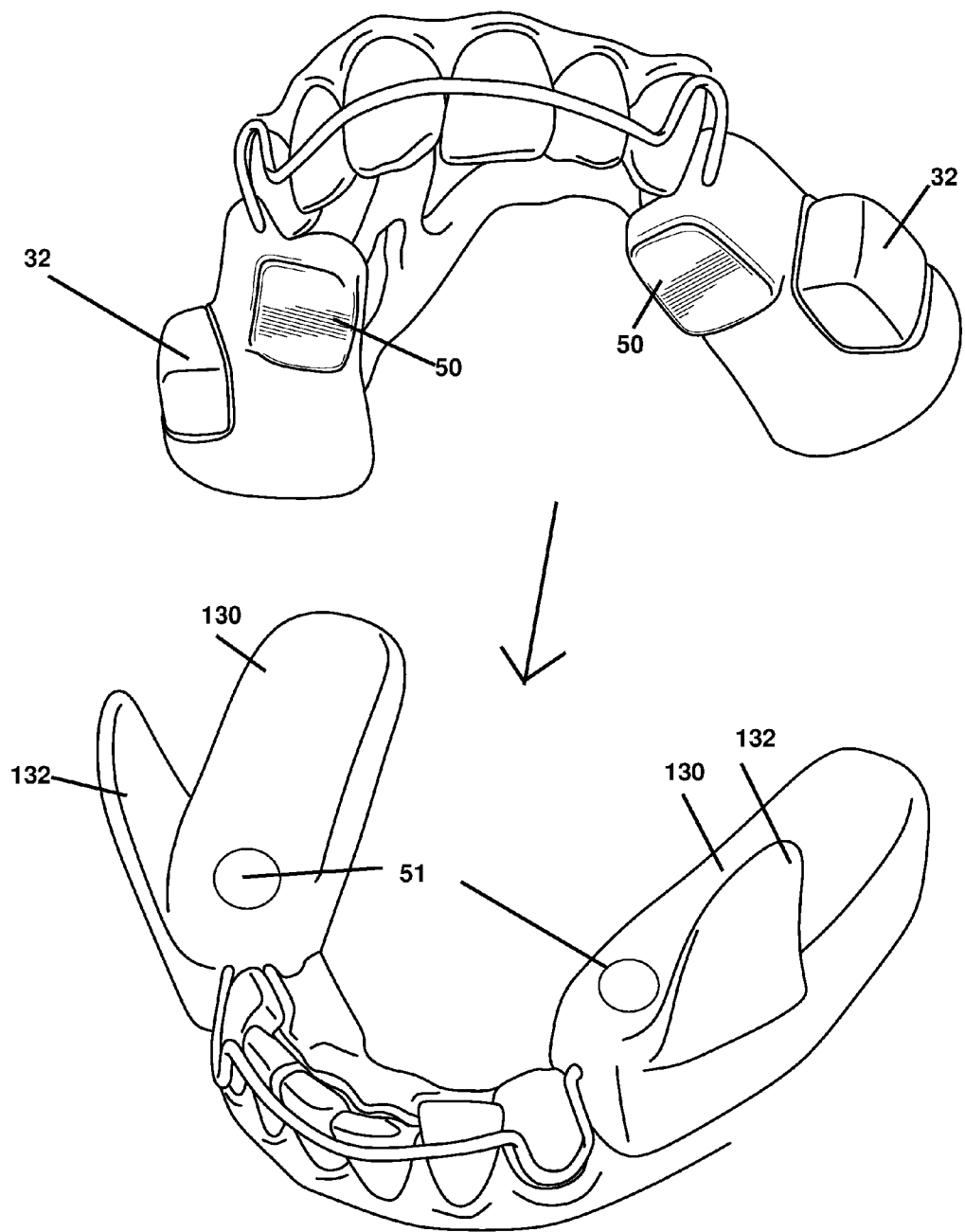
FIG. 11 shows the upper and lower retainers aligned for abutment against each other.

FIG. 11 shows the upper and lower retainers aligned for abutment against each other. Here, the location of contact 51 on the top side and generally elongated flat region 130 of the lower retainer is marked. The lower blocks 50 each contact a respective area of contact 51 on the upper elongated side 130 of the lower retainer. As such, in embodiments, the lower block 50 contacts and abuts the upper elongated side 130 and the side block 32 contact and abuts at its front side, the rear side of the flange 132.

Figure 12:
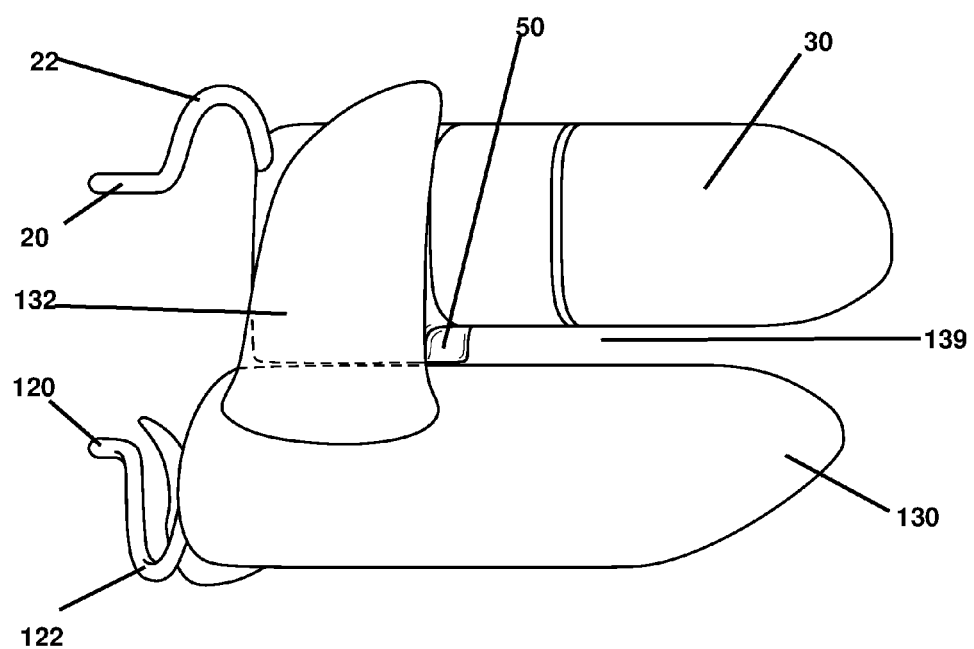
FIG. 12 shows the upper and lower retainers abutted against each other.

FIG. 12 shows the upper and lower retainers abutted against each other. Here, the lower jaw is pushed slightly forward from a natural resting position and the upper jaw is pushed slightly back relative to the lower jaw and a natural resting position. A space or spaced apart region 139, as shown, is formed between the upper retainer and lower retainer behind the upper block 50. This space between the elongated sides 30 and 130 corresponds to any and/or all of the teeth behind the lower block 50, such as the molars and bicuspids.

Figure 13:
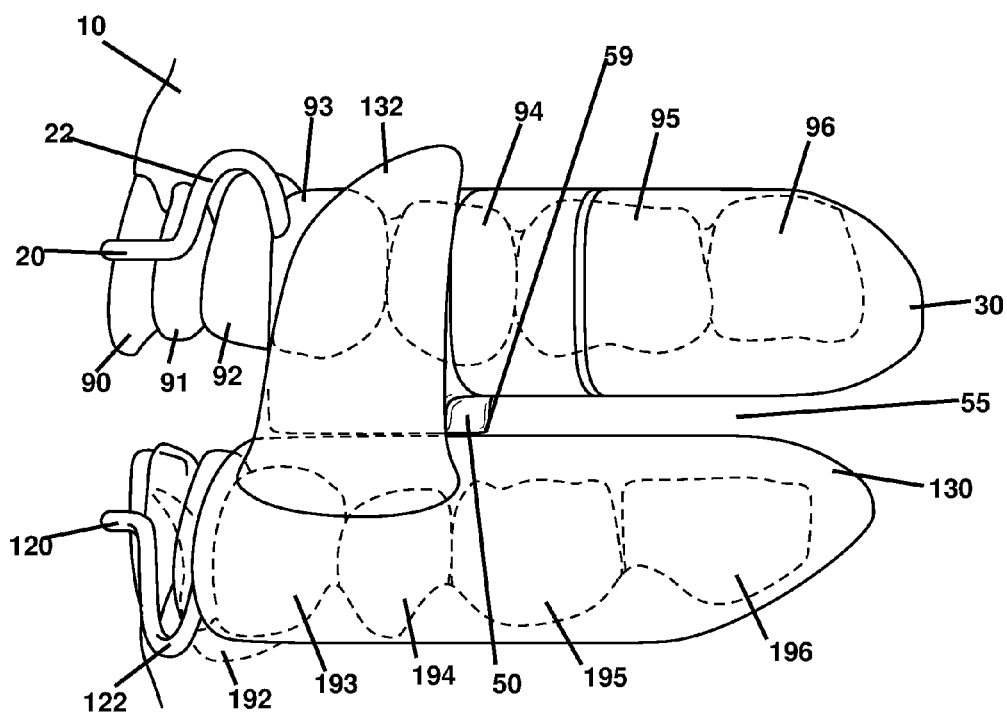
FIG. 13 shows the upper and lower retainers abutted against each other in the mouth of a wearer.

FIG. 13 shows the upper and lower retainers abutted against each other in the mouth of a wearer. Here, the position of the upper retainer having an elongated region 30 and lower retainer having an elongated region 130 are shown. The lower side of the upper retainer is generally flat and faces downwards, such that it is generally parallel to the upper side of the lower retainer which faces upwards with a space 55 between them. This space corresponds to a space created between the upper molars 95, and 96 as well as the lower molars 195, and 196. (Not all molars are shown.) The lower teeth are pushed forward compared to the upper teeth and a rear most point of abutment 59 is created. The wing 132 of the lower retainer, in this embodiment, corresponds to the position of the first 193 and second bicuspids 194 with the canine in front. The lower block 50 corresponds to the position of the first bicuspid 94 and cuspid 93. Additional teeth (incisors, et al) are further shown as teeth 90, 91, 92, and 192.

While the disclosed technology has been taught with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalency of the claims are to be embraced within their scope. Combinations of any of the methods, systems, and devices described hereinabove are also contemplated and within the scope of the invention.

I claim:

1. A retainer system with:
   an upper retainer adapted for abutment against upper teeth, said upper retainer comprising a) a generally flat and elongated lower surface adapted to cover molars and b) lower blocks extending further downwards than said generally flat and elongated lower surface which are adapted to cover canine and first bicuspid teeth; said lower blocks of said upper retainer abutting said lower retainer causing a spaced apart region to be formed between said upper retainer and said lower retainer simultaneous, and
   a lower retainer adapted for abutment against lower teeth, said lower retainer comprising a generally flat and elongated upper surface adapted to cover canine, cuspid, first and second bicuspids, as well as molars.

2. The retainer system of claim 1, wherein said upper retainer and lower retainer abut each other by way of contact between said lower blocks and said generally flat and elongated upper surface.

3. The retainer system of claim 1, wherein a space is formed between said upper retainer and said lower retainer at a region corresponding to said molars and said second bicuspid.

4. The retainer system of claim 3, wherein said lower retainer further comprises wings extending perpendicularly to said generally flat and elongated upper surface.

5. The retainer system of claim 4, wherein said wings abut respective side blocks jutting outwards with front side perpendicular to said generally flat and elongated lower surface.

6. The retainer system of claim 5, wherein a wire on each of said upper retainer and said lower retainer covers at least said incisors.

7. The retainer of claim 1, wherein said lower block has a rear side which is generally, or is, perpendicular to a lower side thereof.

8. The retainer of claim 1 further comprising wings extending from said lower retainer towards said upper retainer adapted to abut respective side blocks on exterior sides of said upper retainer.

9. A retainer system with abutting upper retainer and lower retainer, comprising:
 a spaced apart region between areas of said upper retainer and said lower retainer configured to correspond to molars of teeth that said retainers are adapted to cover;
 contact points between said upper retainer and said lower retainer at regions of said retainer system configured to correspond to a first bi-cuspid where said upper retainer and lower retainer are in contact when said spaced apart region which extends between areas of said upper retainer and said lower retainer corresponding to said molars of said teeth that said retainers are adapted to cover.

10. The retainer system of claim 9, wherein said spaced apart region further comprises a region corresponding to second bi-cuspid.

11. The retainer system of claim 10, wherein said contact points further comprise regions corresponding to said cuspids.

12. The retainer system of claim 11, wherein said lower retainer further comprises vertically extending wings.

13. The retainer system of claim 12, wherein said upper retainer further comprises blocks extending outwards at said spaced apart region, each with a generally flat front surface.

14. The retainer system of claim 13, wherein each wing of said wings abuts a generally flat front surface of a block of said blocks.

15. The retainer system of claim 9, wherein said contact points of said upper retainer are at a lowest most extremity of said upper retainer at a block extending downwards further than a rest of said upper retainer.

16. The retainer system of claim 15, wherein said contact points of said lower retainer on one of two generally flat elongated surfaces extend from a wire to an area corresponding to a molar.

17. The retainer of claim 9, wherein said spaced apart region is terminated at a rear most point of abutment of said upper retainer and said lower retainer.

* * * * *